United States Patent
Equipart

(10) Patent No.: US 8,337,887 B2
(45) Date of Patent: Dec. 25, 2012

(54) RAPIDLY DISINTEGRATING TASTE-MASKED TABLET

(75) Inventor: Paul Equipart, Quaedypre (FR)

(73) Assignees: Laboratories Pharmaceutiques Rodael, Bierne (FR); Laboratories Nutriset, Malaunay (FR)

(*) Notice: Subject to any disclaimer, the term of this patent is extended or adjusted under 35 U.S.C. 154(b) by 1103 days.

(21) Appl. No.: 10/592,408

(22) PCT Filed: Mar. 11, 2004

(86) PCT No.: PCT/EP2004/003663
§ 371 (c)(1),
(2), (4) Date: Sep. 11, 2006

(87) PCT Pub. No.: WO2005/094843
PCT Pub. Date: Oct. 13, 2005

(65) Prior Publication Data
US 2007/0207205 A1    Sep. 6, 2007

(51) Int. Cl.
*A61K 9/20* (2006.01)
(52) U.S. Cl. ........ 424/464; 424/643; 424/646; 424/638; 424/470; 424/465
(58) Field of Classification Search .......... None
See application file for complete search history.

(56) References Cited

U.S. PATENT DOCUMENTS 6,287,596 B1 * 9/2001 Murakami et al. ............ 424/464
6,475,510 B1   11/2002 Venkatesh et al.
6,740,339 B1 * 5/2004 Ohkouchi et al. ............ 424/464

FOREIGN PATENT DOCUMENTS

EP   0922464   6/1999
EP   1203580   5/2002

OTHER PUBLICATIONS

International Search Report, PCT/EP2005/003288/mailed Apr. 10, 2005.

* cited by examiner

*Primary Examiner* — Robert A Wax
*Assistant Examiner* — Hasan Ahmed
(74) *Attorney, Agent, or Firm* — Frost Brown Todd LLC

(57) ABSTRACT

The present invention concerns a rapidly disintegrating taste-masked tablet having both hardness and non-friability properties comprising at least one active principle selected from the group of mineral salts, vitamins and mixtures thereof, the active principle being coated by a sweetening agent wherein the weight ratio of the active principle to the sweetening agent is from 0.2 to 3, and starch and microcrystalline cellulose in a weight ratio of starch to microcrystalline cellulose from about 0.76 to 0.85, and at least one free flow aid. It also concerns a method for the preparation of such a tablet.

16 Claims, No Drawings

RAPIDLY DISINTEGRATING TASTE-MASKED TABLET

The present invention concerns a rapidly disintegrating taste-masked tablet, having both hardness and non-friability properties, and including an active principle, such as iron or zinc salts.

It also concerns a method for the preparation of such a tablet.

In the context of the present invention, "rapidly disintegrating tablet" is understood to mean a tablet which disintegrates in less than 60 s, preferably around 30 s, when placed either in the mouth or else in a small amount of water, as measured according to test A. Test A consists in placing a tablet in a spoon of water (5 ml) at room temperature, and in visually measuring the time for complete disintegration.

In the context of the invention, "non-friability properties" means a friability of less than 5%, preferably less than 3%, and more preferably less than 1%, as measured according to test B, which is described in the European Pharmacopoeia, $4^{th}$ Edition, (4-8) monography, 2.9.7.

In the context of the present invention, "hardness properties" means a compressive strength of not less than 50 N as measured according to test C, which is described in the European Pharmacopoeia, $4^{th}$ Edition, (4-8) monography, 2.9.8.

When an active principle must be orally administered, a difficulty lies in its taste. Indeed, the taste of some active principles is unpleasant, in particular when in doses sufficient to obtain the desired therapeutic effects (i.e. doses of several milligrams per tablet). For instance, mineral salts such as iron or zinc salts, or vitamins such as vitamin B9 (folic acid) pose the problem of unpleasant taste when they have to be supplied to humans, and in particular to children.

In the context of the treatment of diarrhea and other illnesses needing mineral salts supplementation, particularly among children in developing countries, zinc supplements are often prescribed in order to significantly reduce the severity of diarrhea and the duration of the episode ("Effect of Zinc Supplementation on Clinical Courses of Acute Diarrhea", Report of a meeting, New Delhi, 7-8 May 2001, Journal of Health and Population and Nutrition, 2001 December; 19(4), 328-346; BHATTA et al., "Prevention of diarrhea and pneumonia by zinc supplementation in children in developing countries—pooled analysis of randomized trials", Zinc Investigator's Collaborative Group, Journal of Pediatrics, 1989, 135(6), 689-697.

In this particular context, it is very important that zinc supplementation becomes a routine practice. This is only possible if the families can have zinc supplements available to be used as soon as needed, in which the nasty taste of the zinc has been masked in order to avoid rejection of said supplements by the children.

Generally, zinc supplements are used in form of syrups containing sugar. However, in order to mask the taste of the zinc, a high amount of sugar is needed, and the taste is not completely masked in such a galenic form. Furthermore a large amount of syrup has to be administered to obtain the required dosage.

Medicines containing an iron salt or a zinc salt as active principle are generally presented in the form of a tablet that is coated (sugar-coated) or provided with a skin so that the problem of unpleasant taste of the iron salts does not arise for such medicines. In fact, these medicines are destined to be swallowed. Such swallowable medicines cannot be used for treating young children. Furthermore, it is well known that many patients, in particular elderly people, have difficulties in swallowing, and that in order to comply with the treatment, it is highly preferable to propose another administration route.

Therefore, the object of the present invention is to propose a particular formulation of a drug containing at least one active principle having an unpleasant taste, which is above all of acceptable taste, easy to administer and easy to store.

More precisely, the objective of the present invention is attained by producing a rapidly disintegrating taste-masked tablet, which comprises:

at least one active principle selected from the group comprising mineral salts, vitamins, and mixtures thereof, at least one sweetening agent, preferably a low calorie and anticariogenic sugar substitute selected from the group comprising saccharin, cyclamate, aspartame, acesulfame K and alimate, preferably aspartame, optionally at least one flavouring agent, preferably an artificial flavouring agent, starch and microcrystalline cellulose, which are binding agents with disintegrating properties, at least one free flow aid, preferably colloidal silicon dioxide, and at least one lubricating agent, selected from the group comprising magnesium stearate, micronized stearic acid and talc, preferably magnesium stearate, characterized in that:

the active principle is coated by the sweetening agent, and optionally, the flavouring agent, the weight ratio of the sweetening agent to the active principle ranges from 0.2 to 3, preferably from 0.2 to 2.1, and more preferably from 0.6 to 1.8, the weight ratio of starch to microcrystalline cellulose ranges from about 0.76 to about 0.85, and is preferably about 0.8.

The active principle of the present invention is selected from the group comprising mineral salts, vitamins, and mixtures thereof.

The vitamins of the present invention may comprise carotenoids, vitamin E, vitamine D3, vitamine C, thiamine, riboflavin, niacin, folic acid, pyridoxine, biotin, pantothenic acid, and cyanocobalamin. The vitamins of the present invention may preferably comprise fat soluble vitamins such as vitamins A, D, E, and K.

The mineral salts of the present invention comprise salts of minerals which are needed in large amounts, such as calcium, magnesium, potassium, sodium, chlorine, phosphorous; and salts of trace elements which need to be present only in small amounts such as aluminium, copper, cobalt, iron, zinc, vanadium, manganese, iodine, fluorine and selenium.

The mineral salts of the present invention are preferably metallic salts in which:

the salt is selected from the group comprising chlorides, sulphates, sulphites, (hydrated) oxides, (pyro)phosphates, (bi)carbonates citrates and nitrates, preferably sulphates, and mixtures thereof, the metal is selected in the group comprising iron, zinc, copper and magnesium.

The iron salt may either be a ferrous salt such as iron sulphate, iron pyrophosphate and iron oxide, or else a ferric salt such as ferric chloride and ferric pyrophosphate. The preferred iron salt according to the invention is ferrous sulphate.

The preferred zinc salt according to the invention is zinc sulphate. By way of example, zinc sulphate can be extra pure zinc sulphate monohydrate from MERCK.

Zinc sulphate and iron sulphate are preferred since they have good assimilation properties in blood.

According to another embodiment of the invention, the rapidly disintegrating taste-masked tablet may comprise two metallic salts of different metals, for instance iron and zinc sulphates. Preferably, both metallic salts are of the same type.

The sweetening agent is preferably a low calorie and anticariogenic sugar substitute, which is selected from the group comprising saccharin, cyclamate, aspartame, acesulfame K and alitame, and mixtures thereof.

The preferred sugar substitute has a mean diameter of less than 100 µm, such as aspartame. By way of example, aspartame can be Nutrasweet® from the Nutrasweet Company or Ajinomoto Aspartame Powder from the AJINOMOTO COMPANY. Aspartame is a sweetening agent in the form of a white powder having a mean diameter of less than 100 µm. Its taste is sweet (about 200 times sweeter than sugar). It does not lead to caries and it is also low in calories. Aspartame is particularly advantageous in the context of the present invention as an agent for masking the taste of active principles such as iron and zinc salts.

In order to achieve the main desired effect (masking the taste of the active principle, mainly in the case of iron or zinc salts), the weight ratio of the sweetening agent to the active principle ranges from 0.2 to 3, preferably from 0.2 to 2.1, and more preferably from 0.6 to 1.8.

The taste-masked tablet according to the invention may optionally comprise a flavouring agent. The flavouring agents that may be used in the tablet of the invention comprise natural or artificial flavouring substances.

The natural flavouring agents (or flavourings) may comprise flavourings which are prepared from essential oils, such as almond or lemon oil; from vanilla; from fresh fruits, or from ginger extracts.

The artificial flavouring agents (or flavourings) may comprise flavourings which are entirely prepared from synthetic organic chemicals such as vanillin, vanillin acetate, vanillin isobutyrate, vanillyl alcohol, vanillyl butylether, vanillyl ethylether, vanillylidene acetone, vanillin erythro-et threo-butan-2,3-diol acetal, ethylvanillin, ethylvanillin β-d-glucopyranoside, ethylvanillin isobutyrate, ethylvanillin propylene glycol acetal, or menthol, menthofurane, p-menthan-2-ol, p-mentha-8-thiol-3-one, p-menth-1,4(8)-dien-3-one, p-menth-1-en-9-al, 1-p-menthene-8-thiol, p-menth-1-en-3-ol, p-menth-3-en-1-ol, p-menth-8-en-1-ol, or from mixtures of essential oils and synthetic organic chemicals.

The artificial flavouring agents may also comprise artificial flavourings of caramel, chocolate, ginger, mint, peppermint, coffee and honey, as well as artificial flavourings, such as lemon, orange, mandarin, grapefruit, passion fruit, mango, apple, banana, peach, apricot, cherry, blackcurrant, wildberry, strawberry, blueberry, raspberry, cranberry, coconut, pineapple, kiwi, walnut, almond and hazelnut flavourings.

Preferably, in the context of the invention, the flavouring agent is an artificial flavouring agent in order to avoid any risk of inserting impurities in the tablet.

The preferred artificial flavouring agent is ethyl vanillin, which is, in the context of the invention, able to mask the characteristic taste associated with iron or zinc salts.

As mentioned above, the binding agents with disintegration properties must comprise a starch and microcrystalline cellulose.

The preferred sources of starch are corn, wheat, rice, potato, tapioca, barley and mixtures thereof. The preferred starch is corn starch.

By way of example, corn starch can be the product produced by AMYLUM EUROPE N.V. and sold by LAMBERT RIVIERE under the name MERITENA 100.

As an example of microcrystalline cellulose that can be used in the taste-masked tablet of the invention, the microcrystalline cellulose of the AVICEL® type may be mentioned, and preferably the microcrystalline cellulose AVICEL® PH 102 from SEPPIC. Mention may also be made of the microcrystalline cellulose of the VIVAPUR® type 102 from RETTENMAIER.

In order to achieve rapid disintegration as defined above according to test A, suitable friability and hardness properties as mentioned above, the weight ratio of starch to microcrystalline cellulose is in the range from about 0.76 to about 0.85, and preferably about 0.80.

In order to improve the flow properties of the powder during the preparation, it is possible to use a free flow aid. The free flow aid may be selected from the group comprising colloidal silicon dioxide and amourphous hydrated silicon dioxide. The free flow aid is preferably constituted by colloidal silicon dioxide.

By way of example, colloidal silicone dioxide may be AEROSIL 200 from DEGUSSA.

The tablet according to the invention also comprises a lubricant for improving the manufacture of the tablet.

As examples of lubricant that may be used in the context of the invention, magnesium stearate, micronized stearic acid, talc and mixtures thereof may be mentioned.

The lubricant is generally in the form of a fine whitish powder and serves to prevent jamming in the dies of the presses when the mixture is subjected to final compression.

By way of example, magnesium stearate may be purchased from COOPER or UNION DERIVAN S.A.

A preferred general formula of the tablet of the invention is as follows:

active principle: from 0.1 to 100 mg, preferably from 25 to 80 mg, and more preferably from 30 to 70 mg, microcrystalline cellulose: from 200 to 300 mg, preferably from 220 to 260 mg, and more preferably about 250 mg, corn starch: from 150 to 260 mg, sweetening agent: from 20 to 100 mg, preferably from 40 to 50 mg, and more preferably about 45 mg, flavouring agent: from 0 to 1 mg, preferably from 0.01 to 0.05 mg, and more preferably about 0.045 mg, lubricating agent: from 0.1 to 5 mg, and preferably about 2.5 mg, free flow aid: from 0.1 to 10 mg, preferably from 0.5 to 5 mg, and more preferably 1 to 1.5 mg.

The invention also concerns a method for the preparation of the taste-masked tablet according to the invention. This method comprises the successive following steps:

a) providing in a blender at least one active principle, b) adding a sweetening agent to the active principle, the weight ratio of the sweetening agent to the active principle ranging from 0.2 to 3, preferably from 0.2 to 2.1, and more preferably from 0.6 to 1.8, and mixing to form a first granular mixture of granules of the active principle coated by the sweetening agent, c) optionally adding a flavouring agent to the first granular mixture, and mixing to form a second granular mixture of granules of the active principle coated by the sweetening agent and the flavouring agent, d) adding starch and microcrystalline cellulose to the second granular mixture if the method comprises the step c) of adding a flavouring agent, or to the first granular mixture if the method does not comprise the step c) of adding a flavouring agent, the weight ratio of starch to microcrystalline cellulose ranging from about 0.76 to 0.85, and being preferably of about 0.8, and mixing to form a third mixture, e) adding a free flow aid to the third mixture, and mixing to form a fourth mixture, f) adding a lubricant to the fourth mixture, and mixing to form a fifth mixture, g) transferring the fifth mixture to a press, and h) compressing to form a tablet.

Preferably the blender used for the mixing steps a) to f) is a twin-shell blender, and the press used for the compressing step h) is a rotary press.

According to a preferred embodiment of the invention, the active principle and the free flow aid are sieved.

The mixing of the sweetening agent and the active principle is performed until homogeneity of the first granular mixture is obtained, preferably from 3 minutes to 10 minutes, and more preferably about 5 minutes.

In the same manner, the mixing of the flavouring agent and the first granular mixture is performed until homogeneity of the second granular mixture is obtained preferably from 3 minutes to 10 minutes, and more preferably 5 minutes.

With regard to the mixing of the starch, the microcrystalline cellulose and the first or second granular mixture, it is performed until homogeneity of the third mixture is obtained, preferably from 5 minutes to 20 minutes, and more preferably about 10 minutes.

It is preferable that the tablets according to the invention be prepared in an atmosphere of less than 40% RH (RH: relative humidity).

The tablets of the invention or obtained according to the method of the invention are 300 to 900 mg, and preferably about 550 mg in weight, and from about 3 to 5 mm, preferably about 4 mm in thickness, and from 7 to 17 mm, preferably about 12 mm in diameter.

The taste-masked tablet of the invention has at least one of the following properties:

a disintegration time ranging from 15 s to 60 s, preferably from 25 s to 35 s, as measured according to test A, a friability of less that 1%, preferably of less than 0.3%, as measured according to test B, a hardness of not less than 50 N, as measured according to test C.

The invention also relates to a premix comprising at least the active principle, the sweetening agent, and optionally the flavouring agent in powdered form, which are necessary for the preparation of the tablet according to the invention.

The invention will be understood more clearly with the aid of the following examples, which are intended to be illustrative and non limitative.

EXAMPLES

In the examples, the following constituents are used:

Active Principles:

Zinc sulphate: extra pure zinc sulphate monohydrate from MERCK

Iron sulfate: from MERCK

Folic acid: from ROCHE

Binding Agents with Disintegrating Properties:

Corn starch: MERITENA 100 produced by AMYLUM EUROPE N.V., and sold by LAMBERT RIVIERE Microcrystalline cellulose: AVICEL PH102 from SEPPIC or VIVAPUR type 102 from RETTENMAIER Sweetening Agent:

Aspartame: Ajinomoto Aspartame Powder from the Ajinomoto Company

Flavouring Agent:

Ethylvanillin: from RHODIA

Lubricant:

Magnesium stearate: the product sold by COOPER or UNION DERIVAN

Free Flow Aid:

Colloidal silicon dioxide: AEROSIL 200 from DEGUSSA

Example 1

Composition of Tablets According to the Invention

The compositions of tablets according to the invention are given in Table I below:

TABLE I

| NAME OF CONSTITUENT | QUANTITY MG/TABLET | | | |
|---|---|---|---|---|
|  | Tablet 1 | Tablet 2 | Tablet 3 | Tablet 4 |
| Zinc sulphate | 54.900 | 27.45 | — | 27.450 |
| Iron sulphate | — | — | 39.063 | 39.063 |
| Folic acid | — | — | 0.0625 | 0.0625 |
| Corn starch | 198.000 | 210.890 | 205.700 | 193.500 |
| Microcrystalline cellulose | 248.000 | 263.610 | 257.130 | 241.880 |
| Aspartame | 46.435 | 45.000 | 45.000 | 45.000 |
| Ethylvanillin | 0.045 | 0.045 | 0.045 | 0.045 |
| Magnesium stearate | 2.500 | 2.500 | 2.500 | 2.500 |
| Colloidal silicondioxide | 1.120 | 1.120 | 1.120 | 1.120 |
| Total weight | 551.000 | 550.615 | 550.621 | 550.621 |
| Thickness (mm) | 4.200 | 4.200 | 4.200 | 4.200 |
| Diameter (mm) | 12.000 | 12.000 | 12.000 | 12.000 |

Example 2

Preparation of Tablets According to the Invention

A batch of tablets of the invention is prepared as described below, the tablets weighing about 550 mg and being of a thickness of about 4 mm, containing respectively:

20 mg of zinc element (corresponding to tablet 1), 10 mg of zinc element (corresponding to tablet 2);

12 mg of iron element (corresponding to tablet 3); and 10 mg of zinc element and 12 mg of iron element (corresponding to tablet 4).

For tablet 1, the method of preparation is as follows:

a) weighing exactly all the constituents of the tablet in order to obtain a total mass of about 80 kg, b) providing in a blender 7971 g of zinc sulphate, c) adding 6742 g of aspartame into the blender containing the zinc sulphate, and granulating for 5 minutes, in order to obtain a homogeneous first granular mixture, d) adding 6.53 g of ethylvanillin into the first granular mixture, and granulating for 5 minutes to form a second granular mixture, e) adding 36007 g of microcrystalline cellulose and 28748 g of corn starch to the second granular mixture and mixing for 5 minutes to obtain a homogenous third mixture, f) adding 162.6 g of colloidal silicon dioxide to the third mixture and mixing to obtain a homogeneous fourth mixture, g) adding 363 mg of magnesium stearate to the fourth mixture, and mixing to obtain a homogenous fifth mixture, h) transferring the fifth mixture to a press, preferably a rotary press, i) compressing of the fifth mixture until a compressive strength of about 70 N is obtained, j) cooling the tables and discharging.

Compression of the final (fifth) mixture may be carried out on a rotary press or an alternative press. Preferably, compression is carried out on a rotary press, such as FROGERAIS MR 20 type rotary compressing machine, or MANESTY ROTA-PRESS.

Tablets 2 are prepared according to the same procedure as used for tablets 1, except the amounts of the constituents which are indicated, for each constituent, in table II.

TABLE II

| NAME OF CONSTITUENT | QUANTITY (g) |
|---|---|
| Zinc sulphate | 3988 |
| Iron sulphate | 0 |
| Folic acid | 0 |
| Corn starch | 30641 |
| Microcrystalline cellulose | 38300 |
| Aspartame | 6538 |
| Ethylvanillin | 6.54 |
| Magnesium stearate | 363 |
| Colloidal silicon dioxide | 162.7 |
| Total mass (g) | 80000 |

Tablet 3 are prepared according to the same procedure as used for tablets 1 and 2, except the amounts of the constituents which are indicated, for each constituent, in table III.

TABLE III

| NAME OF CONSTITUENT | QUANTITY (g) |
|---|---|
| Zinc sulphate | 0 |
| Iron sulphate | 5675 |
| Folic acid | 9.08 |
| Corn starch | 29886 |
| Microcrystalline cellulose | 37359 |
| Aspartame | 6538 |
| Ethylvanillin | 6.54 |
| Magnesium stearate | 363 |
| Colloidal silicon dioxide | 162.7 |
| Total mass (g) | 80000 |

Tablets 4 are prepared according to the same procedure as used for tablets 1, 2 and 3, except the amounts of the constituents which are indicated, for each constituent, in table IV.

TABLE IV

| NAME OF CONSTITUENT | QUANTITY (g) |
|---|---|
| Zinc sulphate | 3988 |
| Iron sulphate | 5675 |
| Folic acid | 9.08 |
| Corn starch | 28114 |
| Microcrystalline cellulose | 35143 |
| Aspartame | 6538 |
| Ethylvanillin | 6.54 |
| Magnesium stearate | 363 |
| Colloidal silicon dioxide | 162.7 |
| Total mass (g) | 80000 |

Example 3

Properties of Tablets According to the Invention

The properties of the tablets according to the invention are given in table V and have been measured according to the following methods:

"friability": according to test B (European Pharmacopoeia 2.9.7);

"hardness": according to test C (European Pharmacopoeia 2.9.8);

disintegration is determined according to test A: a tablet is placed in a spoon of water (5 ml) at room temperature and the time until its complete disintegration as visually observed is measured as the disintegration time The results are presented in Table V below:

TABLE V

| Properties | Tablet 1 | Tablet 2 | Tablet 3 | Tablet 4 |
|---|---|---|---|---|
| Friability (%) | 1< | 1< | 1< | 1< |
| Hardness (N) | >70 | >70 | >70 | >70 |
| Disintegration time (s) | from 25 to 35 | from 23 to 29 | from 25 to 34 | from 26 to 34 |

The invention claimed is:

1. A taste-masked tablet which disintegrates in less than 60 seconds when placed in a spoon of water (5 ml) at room temperature, said tablet consisting essentially of:
   at least one active principle selected from the group consisting of mineral salts, vitamins, and mixtures thereof,
   at least one sweetening agent selected from the group consisting of saccharin, cyclamate, aspartame, acesulfame K and alitame, and mixtures thereof,
   optionally at least one flavouring agent,
   starch and microcrystalline cellulose, which are binding agents and constitute the sole agents with disintegrating properties in the tablet,
   at least one free flow aid, and
   optionally at least one lubricating agent, selected from the group consisting of magnesium stearate, micronized stearic acid, talc, and mixtures thereof,
   characterized in that:
   the active principle is coated solely by the sweetening agent, and optionally, the flavouring agent,
   the weight ratio of the sweetening agent to the active principle ranges from about 0.2 to about 2.1,
   the weight ratio of starch to microcrystalline cellulose ranges from about 0.76 to about 0.85.

2. The taste-masked tablet according to claim 1, characterized in that the active principle is a mineral salt, in which:
   the salt is selected from the group consisting of chlorides, sulphates, sulphites, oxides, hydrated oxides, phosphates, pyrophosphates, carbonates, bicarbonates, citrates and nitrates, and mixtures thereof; and
   the metal is selected from the group consisting of iron, zinc, copper, magnesium and mixtures thereof.

3. The taste-masked tablet according to claim 2, characterized in that it comprises two metallic salts of the same type, but of different metals.

4. The taste-masked tablet according to claim 1, characterized in that the sweetening agent is in the form of a powder having a mean diameter of less than 100 μm.

5. The taste-masked tablet according to claim 1, characterized in that the starch is a starch selected from the group consisting of corn, wheat, rice, potato, tapioca, barley starches and mixtures thereof.

6. The taste-masked tablet according to claim 1, characterized in that the flavouring agent is an artificial flavouring agent having a vanilla flavour.

7. The taste-masked tablet according to claim 1, characterized in that the tablet has a friability of less than about 1%, as measured according to test B.

8. The tablet according to claim 1, characterized in that the tablet has a hardness of not less than 50 N, as measured according to test C.

9. The taste-masked tablet according to claim 1, characterized in that the tablet presents a disintegration time ranging from about 15 s to about 60 s, as measured according to test A.

10. The taste-masked tablet according to claim 9, characterized in that the tablet comprises dimensions of from about 3 to about 5 mm in thickness, and from about 7 to about 17 mm in diameter.

11. The taste-masked tablet according to claim 1, characterized in that the tablet weighs from about 300 to about 900 mg.

12. The taste-masked tablet according to claim 1 characterized in that the tablet has the following general formula:
- active principle: from about 0.1 to about 100 mg,
- microcrystalline cellulose: from about 200 to about 300 mg,
- corn starch: from about 150 to about 260 mg,
- sweetening agent: from about 20 to about 100 mg,
- flavouring agent: from 0 to about 1 mg,
- lubricating agent: from about 0.1 to about 5 mg,
- free flow aid: from about 0.1 to about 10 mg.

13. Method for the preparation of the rapidly disintegrating taste-masked tablet according to claim 1, comprising successively the steps of:
- a) providing in a blender at least one active principle,
- b) adding a sweetening agent to the active principle, the weight ratio of the sweetening agent to the active principle ranging from 0.2 to 2.1, and mixing to form a first granular mixture of granules of the active principle coated by the sweetening agent,
- c) optionally adding a flavouring agent to the first granular mixture, and mixing to form a second granular mixture of granules of the principle coated by the sweetening agent and the flavouring agent,
- d) adding starch and microcrystalline cellulose to the second granular mixture if the method comprises the step c) of adding a flavouring agent, or to the first granular mixture if the method does not comprise the step c) of adding a flavouring agent, the weight ratio of starch to microcrystalline cellulose ranging from about 0.76 to about 0.85, and mixing to form a third mixture,
- e) adding a free flow aid to the third mixture, and mixing to form a fourth mixture,
- f) adding a lubricant to the fourth mixture, and mixing to form a fifth mixture,
- g) transferring the fifth mixture to a press, and
- h) compressing to form a tablet.

14. Method according to claim 13 characterized in that the granulating step (b) is performed until the first granular mixture is homogeneous.

15. Method according to claim 13, characterized in that the mixing of step (c) is performed until the second granular mixture is homogeneous.

16. Method according to claim 13, characterized in that the mixing of step (d) is performed until the third mixture is homogeneous.

* * * * *